United States Patent [19]
Smith

[11] Patent Number: 5,873,884
[45] Date of Patent: Feb. 23, 1999

[54] SURGICAL CUTTING IMPLEMENT DISPENSER

[75] Inventor: Graham Smith, Plaistow, N.H.

[73] Assignee: Smith & Nephew, Inc., Andover, Mass.

[21] Appl. No.: 928,915

[22] Filed: Sep. 12, 1997

Related U.S. Application Data

[62] Division of Ser. No. 456,648, Jun. 2, 1995, Pat. No. 5,690,659.

[51] Int. Cl.[6] .................................................. A61B 17/32
[52] U.S. Cl. ............................................ 606/167; 606/170
[58] Field of Search ........................... 606/1, 170, 180, 606/167, 15; 29/602.08

[56] References Cited

U.S. PATENT DOCUMENTS

| | | | |
|---|---|---|---|
| 3,983,868 | 10/1976 | Ring | 128/263 |
| 4,895,559 | 1/1990 | Shippert | 604/15 |
| 5,320,635 | 6/1994 | Smith | 606/180 |
| 5,388,589 | 2/1995 | Davis | 128/754 |
| 5,479,936 | 1/1996 | Nabai et al. | 128/754 |
| 5,554,154 | 9/1996 | Rosenberg | 606/80 |
| 5,571,180 | 11/1996 | Blom | 623/9 |

*Primary Examiner*—Michael Buiz
*Assistant Examiner*—Daphna Shai
*Attorney, Agent, or Firm*—Fish & Richardson P.C.

[57] ABSTRACT

A cutting implement dispenser for use with surgical instruments having replaceable cutting implements includes a support structure on which a replacement implement is carried. Operating a release mechanism movably attached to the support releases the implement from the support.

7 Claims, 3 Drawing Sheets

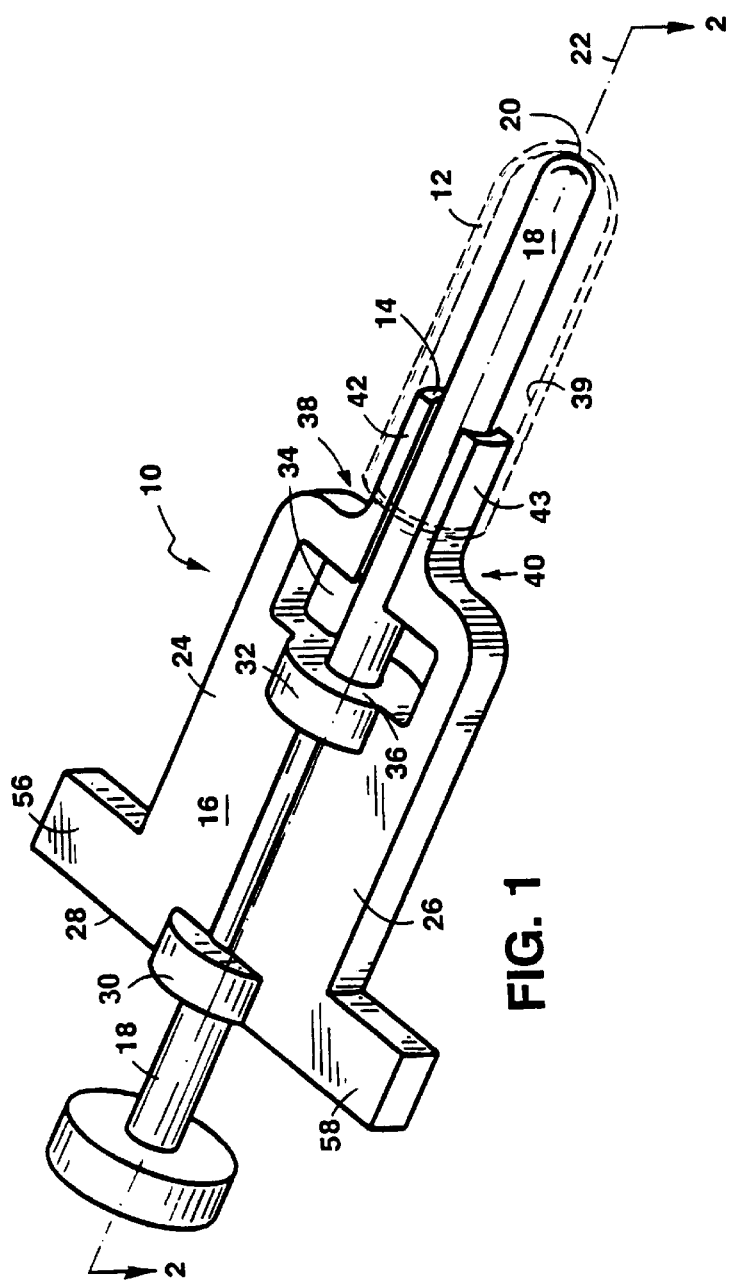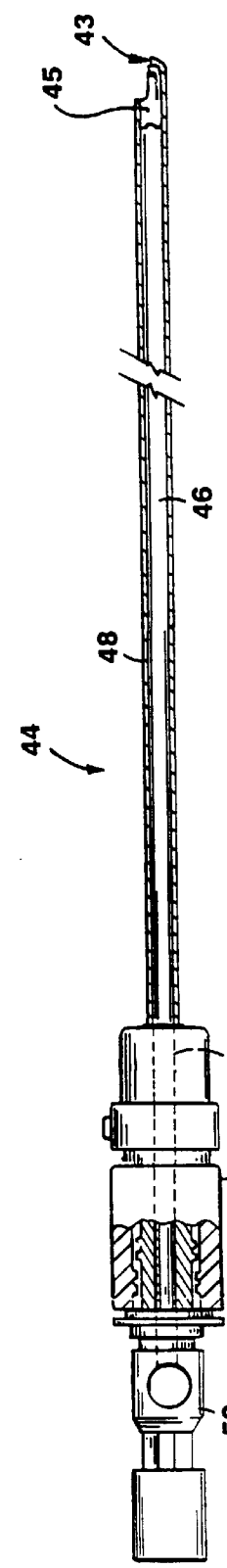

5,873,884

SURGICAL CUTTING IMPLEMENT DISPENSER

This is a divisional of application Ser. No. 08/456,648 filed Jun. 2, 1995 now U.S. Pat. No. 5,690,659.

BACKGROUND OF THE INVENTION

This invention relates to surgical instruments, and in particular to surgical instruments having replaceable cutting implements.

Surgical instruments, for example for arthroscopy, typically include an inner drive member that rotates within an outer member (e.g., a tube). A cutting implement (e.g., a blade or a burr) carried at the distal end of the inner member cuts tissue that extends through a window located at or near the distal end of the outer member.

In some instruments the cutting implement is removably connected to the distal end of the inner member, allowing just the implement to be replaced should it become worn, contaminated, or otherwise unusable. Such a surgical instrument is for example disclosed in U.S. Pat. No. 5,320,635, entitled "Surgical Device With Surgical Element Removably Connected to Drive Element," assigned to the present assignee and incorporated herein by reference in its entirety.

To replace a removably connected cutting implement, the inner drive member is usually first withdrawn from the outer member and the old implement either dislodged from within the outer member or separated from the distal end of the inner member. Typically using a pair of tweezers, an operator (e.g., a surgeon or a nurse) then picks up a replacement implement and drops it into the outer member. The instrument is reassembled by reinstalling the inner member into the outer member.

SUMMARY OF THE INVENTION

One general aspect of the invention is a cutting implement dispenser in which the implement can be disengaged from a support on which it is carried by operating a release mechanism movably attached to the support. Another general aspect of the invention is a method for replacing cutting implements using such a dispenser.

Among other advantages, the invention greatly facilitates the handling of the replacement implement. The replacement implement is often quite small, and thus can be difficult not only to pick up, but also to orient properly in the outer tube (i.e, with the portion of the implement that mates with the inner drive member directed towards the proximal end of the outer tube). Because the replacement implement is carried on a support in the dispenser, the operator can introduce the implement into the outer member by simply orienting the dispenser so that the implement is in the distal end of the outer tube, and operating the release mechanism. The dispenser thus reduces the fumbling and difficulty involved in transporting the replacement implement (e.g., from its sterile packaging) to the instrument and introducing it into the outer member.

The invention also enables an operator to replace an implement without coming into direct physical contact with the new implement. Reducing or eliminating direct physical contact with the replacement implement decreases the likelihood that the operator will contaminate and/or be inadvertently cut by the implement—which is typically sharpened and sterilized prior to packaging.

Preferred embodiments include the following features.

In a particularly useful embodiment, the support structure comprises a pair of radially outwardly biased fingers that engage an inner wall of the cutting implement. A plunger disposed between the fingers is slidably attached to the dispenser body, and is configured so as to extend into the hollow interior of the cutting implement and contact the inner wall when slid with respect to the body.

Other features and advantages of the invention will become apparent from the following detailed description, and from the claims.

BRIEF DESCRIPTION OF THE DRAWINGS

FIG. 1 shows a surgical cutting implement dispenser.

FIG. 3 is a partially cut away side view of a surgical instrument having a replaceable cutting implement.

DESCRIPTION OF THE PREFERRED EMBODIMENTS

Figure 2:
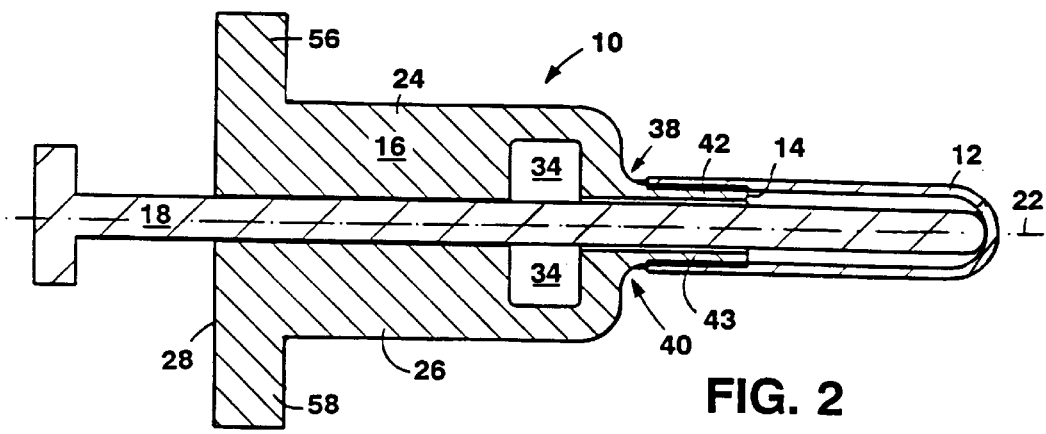
FIG. 2 is a sectional view of the cutting implement dispenser, taken along line 2—2 in FIG. 1.

A cutting implement dispenser 10 for dispensing a replacement cutting implement 12 into a surgical instrument 44 (FIG. 3) is shown in FIGS. 1 and 2. Cutting implement 12 is releasably carried at the distal end 14 of a body 16 comprised of, e.g., polycarbonate, polyethermide, or ABS plastic. A plunger 18, the distal tip 20 of which engages implement 12, extends along a longitudinal axis 22 of body 16. Plunger 18, which is comprised of, e.g., polycarbonate, polyethermide, or stainless steel, may be slid distally with respect to body 16 along axis 22 to release implement 12. If comprised of plastic, body 16 and plunger 18 may be manufactured using standard injection-molding techniques.

Body 16 is split along nearly its entire length into two symmetric halves 24, 26 joined at the proximal end 28 of body 16 by a first annular bridge 30, and midway along body 16 by a second annular bridge 32. Except where it passes through bridges 30, 32, portions of plunger 18 are exposed along the entire length of body 16. Immediately distal of second bridge 32, body 16 defines a rectangular void 34, exposing the distal face 36 of second bridge 32. The portion of each half 24, 26 of body 16 that lies distal of the distal face 36 of second bridge 32 comprises a flexible, cantilevered beam 38, 40. The flexibility of beams 38, 40 can be tailored as desired by, among other things, changing the material of which body 16 is made and/or varying the dimensions of rectangular void 34.

The distal regions of beams 38, 40 define a pair of resilient, radially outwardly biased fingers 42, 43 that frictionally engage the inner surface 39 of implement 12. With cutting implement 12 removed, the width across fingers 42, 43 is slightly larger than the inside diameter of implement 12. For example, if the inside diameter of the implement is 0.105 in. (0.267 cm.), it has been found that an uncompressed width across the outer surfaces of fingers 42, 43 of 0.116 in. (0.295 cm.) provides sufficient frictional engagement to hold implement 12 in place when dispenser 10 is, e.g., moved from its sterile package (not shown) to instrument 44, but yet not so much friction as to make it unduly difficult to release implement 12 using plunger 18.

A surgical instrument 44 having a replaceable cutting implement 45 at its distal end 43 is shown in FIG. 3. Cutting implement 45 mates with and is driven by an inner tube 46, which rotates within a stationary outer tube 48. The proximal end of inner tube 46 is coupled to a hub 50, which is rotatably (and releasably) received within a cavity 52 (FIGS. 4 and 5) in a base 54 attached to the proximal end of outer tube 48.

It may be desirable to replace cutting implement 45 after each use of instrument 44 (e.g., because of contamination concerns), or when implement 45 becomes worn, damaged, or otherwise unusable. To replace the implement, inner tube 46 is first withdrawn from outer tube 48. Implement 45 is then either dislodged from within outer tube 48, such as by upending the tube, or separated from the distal end of the inner tube 46. Implement 45 is then typically discarded.

Figure 4:
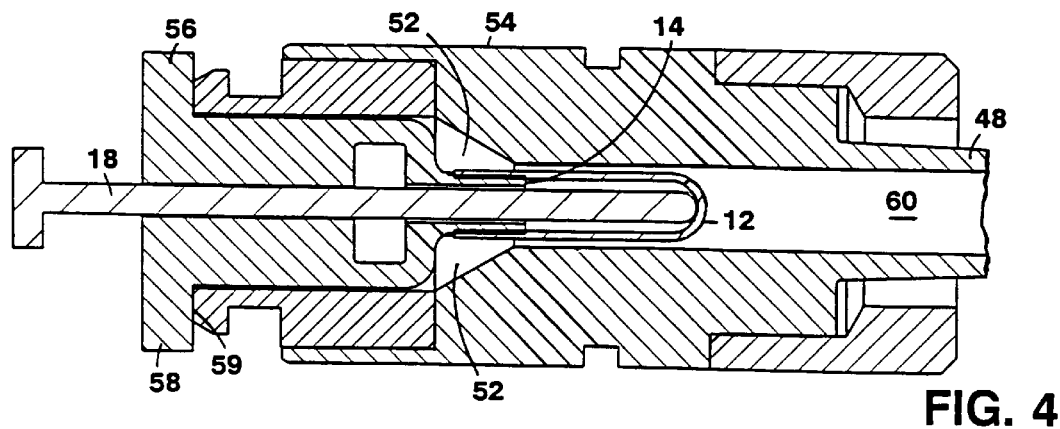
FIG. 4 is a sectional view showing the cutting implement dispenser inserted into the proximal end of the surgical instrument.
Figure 5:
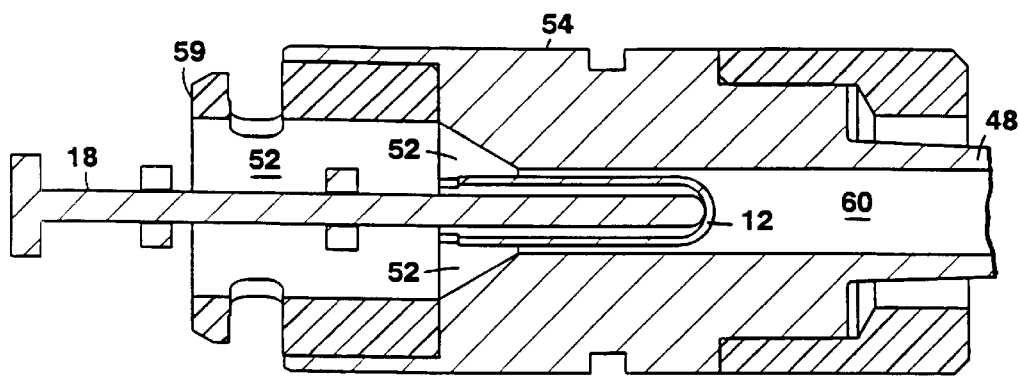
FIG. 5 is a sectional view, taken along a section line perpendicular to the section line along which the view shown in FIG. 4 was taken, showing the cutting implement dispenser inserted into the proximal end of the surgical instrument.
Figure 6:
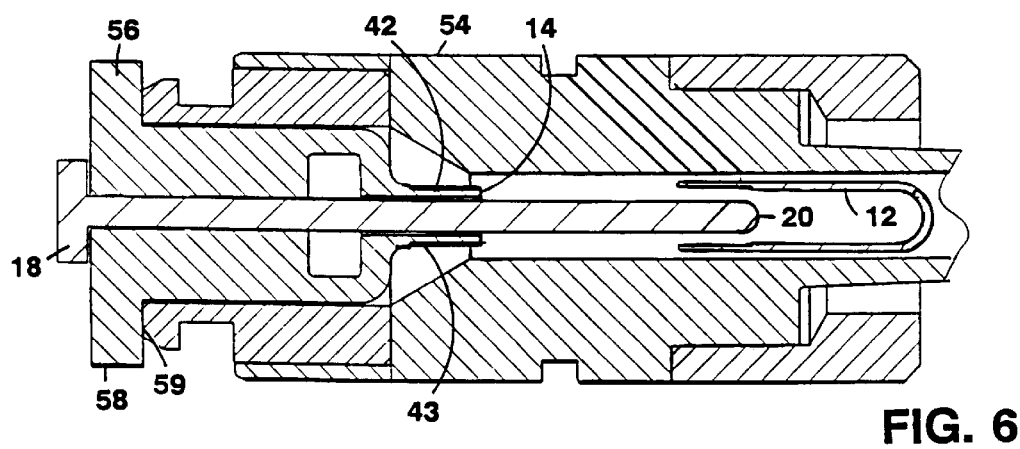
FIG. 6 is a sectional view, taken along the section line along which the view shown in FIG. 4 was taken, showing the cutting implement dispenser inserted into the proximal end of the surgical instrument with the cutting implement released from the dispenser.

With old cutting implement 45 removed, dispenser 10 is inserted, distal end 14 first, into cavity 52, as shown in FIGS. 4 and 5. A pair of lobes 56, 58 extending laterally from the proximal end 28 of body 16 engage the proximal end 59 of base 54, preventing body 16 from extending too far into the instrument. At this point, replacement implement 12 lies almost completely within the hollow passage 60 defined by outer tube 48. With the distal end 43 of instrument 44 pointed downward, plunger 18 is then pushed distally along axis 22 to release cutting implement 12 from fingers 42, 43, as shown in FIG. 6. Dispenser 10 is then removed from cavity 52 and inner tube 46 reinserted into outer tube 48, where it engages implement 12.

Dispenser 10 can be recycled by installing a new implement over fingers 42, 43, or can instead be discarded after a single use. Dispenser 10 and implement 12 are typically sterilized and packaged together.

Other embodiments are within the scope of the following claims.

For instance, the surgical cutting implement need not be hollow like implement 12. Rather, the implement may be solid, in which case the fingers can be biased radially inward to releasably engage the outer surface of the implement.

Nor must the implement, solid or hollow, be carried by a pair of fingers cantilevered from the dispenser body. The implement could instead engage either the inner surface or the outer surface of a tubular sheath extending from the body.

It is also not necessary to use a plunger to release the cutting implement from the body. For instance, if the implement is held in place by fingers (which can be, e.g., flexibly coupled to the body such as fingers 42, 43 or hinged with respect to the body), the implement could be released by a mechanism that either forces the fingers radially inward (e.g., if the fingers are biased outward to engage an inner surface of the implement), or forces them radially outward (e.g., if the fingers are biased inward to engage an outer surface of the implement).

What is claimed is:

1. A method of replacing a first surgical instrument cutting implement removably connected to the distal end of an inner drive member disposed within an outer member, said method comprising:

withdrawing the inner drive member from the outer member;

disconnecting the first cutting implement from the distal end of the inner drive member;

providing a dispenser comprising:
a second surgical instrument cutting implement;
a support structure releasably engaged with said second cutting implement, said support structure including a release mechanism for disengaging said second cutting implement from said support structure;

orienting said dispenser to position said second cutting implement at a proximal end of the outer drive member;

operating said release mechanism to disengage said second cutting implement from said support structure; and reinserting the inner drive member into the outer member.

2. The method of claim 1 wherein said release mechanism comprises a plunger slidably attached to said support structure.

3. The method of claim 2 wherein said operating step comprises sliding said plunger with respect to said support structure.

4. The method of claim 2 wherein said plunger is configured to contact said second cutting implement when said plunger is slid with respect to said support structure.

5. The apparatus of claim 2 wherein said plunger is configured to extend into a cavity defined by the inner wall of said second cutting implement when said plunger is slid with respect to said support structure.

6. The method of claim 1 wherein said support structure includes a pair of radially outwardly biased fingers configured to engage an inner wall of said second cutting implement.

7. The apparatus of claim 5 wherein a plunger is disposed between said fingers.

* * * * *